(12) United States Patent
Gray et al.

(10) Patent No.: US 11,549,199 B2
(45) Date of Patent: *Jan. 10, 2023

(54) ACTIVE APPAREL AND FABRIC AND COVERINGS

(71) Applicants: David A. Gray, St. Paul, MN (US); Mark A. Litman, Edina, MN (US)

(72) Inventors: David A. Gray, St. Paul, MN (US); Mark A. Litman, Edina, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/831,510

(22) Filed: Jun. 3, 2022

(65) Prior Publication Data
US 2022/0298674 A1 Sep. 22, 2022

Related U.S. Application Data (63) Continuation of application No. 15/709,448, filed on Sep. 19, 2017, now Pat. No. 11,352,715.

(51) Int. Cl.
| | | |
|---|---|---|
| *D01F 1/10* | (2006.01) | |
| *D06M 13/46* | (2006.01) | |
| *D06M 16/00* | (2006.01) | |
| *D06M 13/48* | (2006.01) | |
| *F16D 9/08* | (2006.01) | |
| *D06M 13/148* | (2006.01) | |
| *B64D 45/00* | (2006.01) | |

(52) U.S. Cl.
CPC ............ *D01F 1/10* (2013.01); *D01F 1/103* (2013.01); *D06M 13/148* (2013.01); *D06M 13/46* (2013.01); *D06M 16/00* (2013.01); *F16D 9/08* (2013.01); *B64D 45/00* (2013.01)

(58) Field of Classification Search
CPC ....... D01F 1/103; D06M 16/00; D06M 13/46; D06M 13/148
See application file for complete search history.

(56) References Cited

U.S. PATENT DOCUMENTS

| | | | |
|---|---|---|---|
| 5,622,168 A * | 4/1997 | Keusch | A61B 5/282 607/152 |
| 11,352,715 B2 * | 6/2022 | Gray | D06M 13/148 |
| 2006/0004336 A1 * | 1/2006 | Zhang | A61L 15/60 604/368 |
| 2007/0225663 A1 * | 9/2007 | Watt | A61M 1/915 602/42 |

* cited by examiner

*Primary Examiner* — Jeremy R Pierce
(74) *Attorney, Agent, or Firm* — Mark A. Litman & Associates, P.A.

(57) ABSTRACT

A fabric delivers active ingredients to a surface when the fabric includes a moist-vapor porous combination of fabric materials, and the fabric comprises at least 0.5% by total weight of at least one layer of the fabric of a superabsorbent polymer fiber. The superabsorbent polymer fiber contains an absorbed aqueous reservoir of an aqueous solution carrying the active ingredients. The superabsorbent fiber has a coating on its surface of an aqueous penetrable layer through which a liquid in the absorbed aqueous reservoir can migrate or flow, carrying the active ingredients onto an exposed surface of the superabsorbent polymer fiber, so that the active ingredients on the surface of the superabsorbent polymer can react or interact with an environment in contact with the active ingredients on the superabsorbent polymer fiber surface.

16 Claims, 2 Drawing Sheets

ACTIVE APPAREL AND FABRIC AND COVERINGS

RELATED APPLICATIONS DATA

This application claims priority under 35 U.S.C. 120 as a Continuation of U.S. patent application Ser. No. 15/709,448, filed 19 Sep. 2017 and titled ACTIVE APPAREL AND FABRIC AND COVERINGS, now U.S. Pat. No. 11,352, 715, which in turn claims priority as a Continuation-in-Part from U.S. patent application Ser. No. 12/977,291 filed 23 Dec. 2010 and titled ANTIMICROBIAL APPAREL AND FABRIC AND COVERINGS, now U.S. Pat. No. 9,901,128, which in turn claims priority from U.S. Provisional Application 61/284,772, filed Dec. 24, 2009, and from U.S. Provisional Application 61/398,949, filed Jul. 2, 2010. These applications are incorporated herein by reference in their entireties.

BACKGROUND OF THE INVENTION

1. Field of the Invention

The present invention relates to drapable, wrappable and donnable apparel. In particular, the invention relates to articles for controlling the spread of pathogens and infectious materials.

2. Background of the Art

In recent years, fabrics have been designed to provide benefits beyond merely warmth, protection from the elements and fashion. Fabrics have been used to allegedly increase the rate of weight loss, provide muscle support during exercise, and even include electronics to measure body functions and enhance sport training. Published U.S. Patent Application Document 2007/0044801 and Published U.S. Patent Application Document 2007/0141126 and U.S. Pat. No. 4,856,509 disclose face masks containing antimicrobial ingredients that are used as a first barrier against inhalation of such diseases, usually viruses.

Fabrics have been used in vehicles, wearing apparel and furniture to resist stains, absorb odors and provide heat (through resistance fibers) in the fabric.

Fabrics have been specifically designed for these unique purposes over the years, but there are few generic fabric materials that can cross functional lines. It would be desirable to create a unique fabric that has cross-technology capability.

Superabsorbent polymers (SAP) (also called slush powder) are polymers that can absorb and retain extremely large amounts of a liquid relative to their own mass.

Water absorbing polymers, classified as hydrogels, absorb aqueous solutions through hydrogen bonding with the water molecule. An SAP's ability to absorb water is a factor of the ionic concentration of an aqueous solution. In deionized and distilled water, SAP may absorb 500 times its weight (from 30-60 times its own volume), but when put into a 0.9% saline solution, the absorbency drops to maybe 50 times its weight. The presence of valent cations in the solution will impede the polymers ability to bond with the water molecule.

The total absorbency and swelling capacity are controlled by the type and degree of cross-linking to the polymer. Low density cross-linked SAP generally has a higher absorbent capacity and swell to a larger degree. These types of SAPs also have a softer and more cohesive gel formation. High cross-link density polymers exhibit lower absorbent capacity and swell. The gel strength is firmer and can maintain particle shape even under modest pressure.

In the early 1960s, the United States Department of Agriculture (USDA) was conducting work on materials to improve water conservation in soils. They developed a resin based on the grafting of acrylonitrile polymer onto the backbone of starch molecules (i.e. starch-grafting). The hydrolyzed product of the hydrolysis of this starch-acrylonitrile co-polymer gave water absorption greater than 400 times its weight. Also, the gel did not release liquid water the way that fiber-based absorbents do.

The polymer came to be known as "Super Slurper". The USDA gave the technical know how to several USA companies for further development of the basic technology. A wide range of grating combinations were attempted including work with acrylic acid, acrylamide and polyvinyl alcohol (PVA). Polyacrylate/polyacrylamide copolymers were originally designed for use in conditions with high electrolyte/mineral content and a need for long term stability including numerous wet/dry cycles. Uses include agricultural and horticultural. With the added strength of the acrylamide monomer, used as medical spill control, wire and cable waterblocking properties can be provided.

Copolymer Chemistry

Superabsorbent polymers are now commonly made from the polymerization of acrylic acid blended with sodium hydroxide in the presence of an initiator to form a polyacrylic acid sodium salt (sometimes referred to as sodium polyacrylate). This polymer is the most common type of SAP made in the world today. Other materials are also used to make a superabsorbent polymer, such as polyacrylamide copolymer, ethylene maleic anhydride copolymer, cross-linked carboxy-methyl-cellulose, polyvinyl alcohol copolymers, cross-linked polyethylene oxide, and starch grafted copolymer of polyacrylonitrile to name a few. The latter is one of the oldest SAP forms created.

Today superabsorbent polymers are made using one of two primary methods; suspension polymerization or solution polymerization. Both processes have their advantages over the other and both yield a consistent quality of product.

Solution Polymerization

Solution polymers offer the absorbency of a granular polymer supplied in solution form solutions and can be diluted with water prior to application. Can coat most substrates or used to saturated. After drying at a specific temperature for a specific time, the result is a coated substrate with superabsorbent functionality. For example, this chemistry can be applied directly onto wires & cables, though it is especially optimized for use on components such as rolled goods or sheeted substrates.

Solution based polymerization is the most common process used today for SAP manufacture. This process is efficient and generally has a lower capital cost base. The solution process uses a water based monomer solution to produce a mass of reactant polymerized gel. The polymerization's own reaction energy (exothermic) is used to drive much of the process, helping reduce manufacturing cost. The reactant polymer gel is then chopped, dried and ground to its final granule size. Any treatments to enhance performance characteristics of the SAP is usually accomplished after the final granule size is created.

Suspension Polymerization

The suspension process is practiced by only a few companies because it offers a higher degree of production control and product engineering during polymerization step. This process suspends the water based reactant in a hydrocarbon based solvent. The net result is that the suspension polymerization creates the primary polymer particle in the reactor rather than mechanically in post-reactions stages. Performance enhancements can also be during or just after the reaction stage.

U.S. Pat. No. 7,528,291 (Herfert et al.) describes a color-stable superabsorbent polymer having long-term color stability, and methods of manufacturing the polymer, are disclosed. The color-stable superabsorbent polymer is prepared in the essential absence of a persulfate, and is subjected to a low dose of ultraviolet radiation. The resulting superabsorbent polymer resists color degradation during periods of extended storage, even at an elevated temperature and humidity.

U.S. Pat. No. 5,837,789 (Stockhousen) describes superabsorbing polymers for watery liquids, processes used in their production and their application. The polymers, based on monomers containing carboxylate groups and obtained by a special combination of cross-linking agents and other comonomers, show a combination of properties never attained before with regard to absorption rate, high retention at high absorption under pressure, low soluble content and good permeability of the gel layer for watery liquids under pressure load and stable surface cross-linkage.

U.S. Pat. No. 5,669,894 (Goldman et al.) describes absorbent polymers and materials useful in the containment of fluids, that have at least one region containing hydrogel-forming absorbent polymer in a concentration of from about 60 to 100% by weight and providing a gel-continuous fluid transportation zone when in a swollen state. This hydrogel-forming absorbent polymer has: (a) a Saline Flow Conductivity (SFC) value of at least about $30 \times 10^{-7}$ cm$^3$ sec/g; (b) a Performance under Pressure (PUP) capacity value of at least about 23 g/g under a confining pressure of 0.7 psi (5 kPa); and (c) a basis weight of at least about 10 gsm. In addition, the region where this hydrogel-forming absorbent polymer is present has, even when subjected to normal use conditions, sufficient wet integrity such that the gel-continuous zone substantially maintains its ability to acquire and transport fluids through the gel-continuous zone.

Published U.S. Patent Publication 20040077744 (Naylor) describes a process of preparing water soluble or water swellable polymer comprising the steps: a) forming an aqueous mixture comprising, i) a water soluble ethylenically unsaturated monomer or blend of monomers and, ii) at least one first ultra-violet initiator, iii) at least one second ultra-violet initiator; b) effecting polymerisation by subjecting the aqueous mixture formed in step (a) to irradiation by ultra-violet light at an intensity of up to 1,000 micrometers Wcm.sup.−2; subjecting the product of step (b) to irradiation by ultraviolet light of greater than 1,000 micrometers Wcm.sup.−2, characterised in that a significant amount of the first initiator(s) is/are activated in step (b) and a significant amount of the second initiator(s) is/are activated in step (c). The process is particularly suitable for making highly effective water soluble and water swellable polymers useful as flocculants, coagulants, rheology modifiers, dispersants, superabsorbents and binders etc.

U.S. Pat. No. 7,462,753 (Ma) discloses a nano-silver wound dressing consisting of a skin contact layer made from hydrophilic cloth and directly contacting a wound on the surface of the skin, a disinfecting (or bactericidal) antitoxic layer made from activated charcoal cloth impregnated with nanocrystalline silver, a blood absorbing and styptic layer made from a superabsorbent polymer non-woven cloth, an isolation layer made from a composite fabric with a pore size of less than 5 micrometers and an elastic bandage for fixing a main body on the site of wound. Edges of the isolation layer and the skin contact layer are integrated to form a main body while the disinfecting (or bactericidal) antitoxic layer as well as the blood absorbing and styptic layer are separated from each other and both enclosed inside the main body.

U.S. Pat. No. 6,967,261 (Soereus) describes a bandage or wrap with antibiotics therein. It is further described that an included nonwoven material may be treated to be hydrophilic or may include superabsorbent materials.

U.S. Pat. No. 7,541,395 (Reimann) describes a process for producing an absorbent polymer including a first mixing event, in which a plurality of absorbent polymer particles (1) are mixed with a liquid (2) and a second mixing event, in which the liquid (2) is homogenized within the interior of the polymer particles. The polymer particles (1) in the first mixing event are mixed with a speed such that the kinetic energy of the individual polymer particles (1) is on average larger than the adhesion energy of the individual polymer particles (1), and the polymer particles (1) in the second mixing event are stirred at a lower speed than in the first mixing event. The different speeds effect a fluidization of the polymer particles (1), which prevents a clumping of the polymer particles (1) during the mixing event. The absorbent polymers thus produced are distinguished by a particularly rapid swelling behavior.

All references cited herein are incorporated by reference herein in their entirety for information on polymers, especially SAP materials and antibiotics and fabric processing.

SUMMARY OF THE INVENTION

The system includes a fabric as a platform for carrying out the delivery of "active ingredients" upon demand, the demand often initiated by the introduction of moisture, usually by ambient or environments or bodily moisture. The fabric has been found to provide a unique delivery capability by the SAP retaining an solution including actives, and the presence of ambient moisture, the reduction or increase of levels in levels of ambient moisture, or the complete removal of ambient moisture can adjust the rate of delivery of the actives, and thus control delivery to instructed environmental demands. The material can also provide a platform wherein a flowable internal component (gel, liquid, liquid layer, liquid coating, constant or activatable) provides a platform for maintaining activity in the fabric during use over an extended period of time.

To accomplish this more durable and constantly active or reactivatable antimicrobial agent to the apparel delivery system, the antimicrobial agent may be carried in a medium that remains in the apparel with a controlled viscosity, and the fabric may also include or be coated with a) hygroscopic materials, or b) humectants or c) fluid, film-forming material. The SAP (superabsorbent particles of fibers) is distributed in a single layer, within multiple layers, or sandwiched between layers or in a laminated layer in the fabric structure. The fabric will have at least one layer comprising the SAP which is loaded with the active ingredient that is to be controllably released. This can be accomplished in a number of ways. These ways include 1) using a liquid carrier (aqueous carrier) for the active ingredient in the SAP component of the fabric that is of a desirable viscosity so that even with ambient moisture stimulation/activation, flow at a rate that will not rapidly deplete the actives; 2) there is a discontinuous coating on the SAP which restricts flow off the SAP fiber; or 3) a lugubrious of viscous or humectant liquid coating material on the surface of the SAP component of the fabric that delays or slows or controls molecular transfer from the liquid reservoir of actives within the SAP fiber out of the fiber and through the liquid coating material on the surface of the SAP. This is done so that any ambient moisture, as from breath exhalation, perspiration, tears, mist, rain, melting snow, intentionally sprayed aqueous liquid, spilled liquid and the like. This ambient aqueous moisture provides water/moisture that is retained or used by the composition in the fabric to maintain, initiate, released or reactivate the active material. In this manner, any positioned fabric, as apparel, lining for apparel, wrap, applique, bandage, adhesive bandage, patch, undergarment, hat, sportswear and the like) may be used in its normal fabric fashion. The actives system described herein may be used in any o the embodiments with actives.

The actives may include any antimicrobial material, antiperspirants, anti-odorants, anti-inflammatants, coolants (such as evaporative compounds with high energy of evaporation), specific medications (other than anti-microbials, such as anticoagulants, blood thinners, transdermally deliverable medications) such as analgesics, absorbent powders, lubricants, emollients, UV-absorbers/sunscreens, and the like. Traditional and generally known materials with these active functionalities may be used.

To present the active materials within the fabric material from too rapidly dispersing in an activating aqueous environment, the actives and other agent may be carried in or on an immobilizing material, in addition to the SAP, surface coatings, and viscosity agents, such that the active is exposed to the surface of the SAP fiber and any layers on the SAP fiber surface and is not allowed to too rapidly disperse from the surfaces of the SAP fiber and associated coating layers on the SAP fiber. Because the actives are immobilized, yet constantly active within the material/fabric because of its ability to flow, change its state of activity when contacted by moisture/humidity from ambient conditions or the ambient environment, and it can be used in higher concentrations than those found in sprays on liquid applications.

Two such commonly available QIM's are glycerin, water-soluble solids such as mannitol, rabbitol, water-soluble polymers, high molecular weight water-soluble salts, amphoteric compounds, alkanoates and their salts, intermediate chain length (C10-C18 alkanols, and other materials that had limited but effective water-solubility and some effective but low mobility out of the SAP fabric. The QIM is intended to allow the actives to be mobile within the QIM due to submicroscopic molecular movement (e.g., due to concentration gradients of mass flow of solutions over surfaces, including the liquid coatings) or even microscopic Brownian Movement, such that an effective amount of active is always available at the doped QIM/material release interface as a hydrophilic surface. Surfaces with a contact angle <90 degrees are referred to as hydrophilic and those with an angle >90 degrees as hydrophobic, so the surface of the immobilized actives should have a water contact angle of less than 90 degrees when moisture has activated the agent. Additionally, it may be desirable to create a tortuous pathway that insures that the actives release surface comes in contact with the actives.

The present technology also relates to the preparation of a distinct superabsorbent polymer (SAP) fiber that is combined with conventional textile fibers (including natural and synthetic fibers, and even non-textile fibers such as wood fibers, insoluble cellulosic fibers, glass fibers, ceramic fibers) and an antimicrobial agent. The blending of the SAP fiber into the other fiber materials (within a thread, within a yarn, as a fiber mixed within a non-woven blend), with an antimicrobial agent specifically associated with the SAP fiber, provides an ease of manufacture and an ease of control of the overall properties of a final fabric, including feel, drape, flexibility and antimicrobial activity. It is preferred that the antimicrobial agent be associated specifically with the SAP fiber before association with the other fibers, but because of the increased absorbency of the SAP fibers compared to the other fibers in the final material, after manufacture application is possible.

The SAP fiber concentration in the final product should be from 1 to 50% by total weight of the fabric and the antimicrobial should be present as from 0.25% to 15% by weight of the SAP fiber. The SAP fiber may be uniformly distributed throughout the additional fibers, or may be strategically positioned in discontinuous concentrations or patterns within the final fabric.

In addition to the release of actives, the fabric material with the liquid coating on the surface of the fibers can also filter out particles, including environmental irritants and microbes, even at the viral size level. The treatments to the fabric create filter media according to the present invention will afford the fabric layers with the liquid coated SAP the ability to remove the viruses by creating a more tortuous path of "sticky stuff" (a surface that will hold the virus because of its lower surface tension) while it is actively doped with the antimicrobial.

When we speak of filters or masks, we refer to any filtration material be it in mask form or as part of a more elaborate device whose purpose is the removal of particulate matter from the air.

A few of the possible configurations for application of the actives into the fabric of this this technology are (specifics not given here):

1. a spray dopant to be sprayed on the outer surfaces of fabric masks, such as N95 Masks
2. a modified replaceable cartridge for a mobile CPAP style device;
3. a device that could be employed for buildings, cars, airplanes and alike.

The present invention is directed to a germicidal surface-covering assembly that includes at least one custom (fit for a person) apparel, which may comprise one or more different wrappable, donnable, pullover or drapable garments. Each garment defines at least one treated surface that is susceptible to pathogen contamination in a physical contamination event when used as intended in an environment subject to contamination (e.g., a clinical environment, a laboratory or a workplace) and is treated with an active or activatable hydrophilic environment that may provide even a liquid surface to attract and attach virus particles. The treated surface is typically oriented at least outwardly away from a user's body and toward the environment or the source of contamination.

According to the invention, each treated surface is adapted to provide a rapid-acting, even if time-dependent reduction in the number of pathogens available at that treated surface after a physical contamination event (including especially inhalation through the apparel), such that at least a predetermined time after a physical contamination event at a first location on a first treated surface of a first garment (and optionally a first physical contact between the first location on the first treated surface and a second location on a second treated surface of a second garment) results in fewer viable pathogens on the surfaces as compared to an untreated control.

According to an aspect of the invention, the germicidal surface-covering assembly includes garments may be selected from facemasks, head covers, sweaters (especially turtle necks), scarves or the like that can be readily positioned over the mouth and nasal passages of a wearer.

According to the invention, the surface of the actives or germicidal surface-covering assembly may be treated with an antimicrobial agent that is lethal to microbes (especially a viricide) selected from, but not limited to, one or more of: polyhexamethylene biguanide (PHMB), other biguanide compounds, chlorohexidine, alexidine, and relevant salts thereof, a quaternary ammonium compound, a quaternary siloxane, a polyquaternary amine; metal-containing species and oxides thereof, either in particle form or incorporated into a support matrix or polymer; halogens, a halogen-releasing agent or halogen-containing polymer, a bromo-compound, a chlorine dioxide, a thiazole, a thiocynate, an isothiazolin, a cyanobutane, a dithiocarbamate, a thione, a triclosan, an alkylsulfosuccinate, an alkyl-amino-alkyl glycine, a dialkyl-dimethyl-phosphonium salt, a cetrimide, hydrogen peroxide, 1-alkyl-1,5-diazapentane, cetyl pyridinium chloride, stabilized peroxide, sulfides, bis-phenols, polyphenols, chitosan, anatase $TiO_2$, tourmaline, hydrotropes, chaotropic agents, and synergistic combinations thereof. The germicide may be present on the germicidal garment substrate at a final concentration or add-on in a range of about 0.05-8 weight percent of the apparel or garment material. In addition, there must be a hydrophilic carrier agent for the antimicrobial agent in a weight percent of 0.05 to 8% by weight of the apparel and in proportions with the antimicrobial agent of between 10-90% by total weight of the hydrophilic carrier and the antimicrobial material.

In an aspect of the invention, the actives can be effectively delivered in effective levels of milligrams or micrograms/$cm^2$ as the surface-covering assembly will reduce the contact transfer or indirect transmission from the surface and/or through the apparel to the undesired targets. ingestion passages of the wearer.

Additional features and advantages of the present protective and/or sanitizing articles and associated methods of manufacture will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Figure 1A:
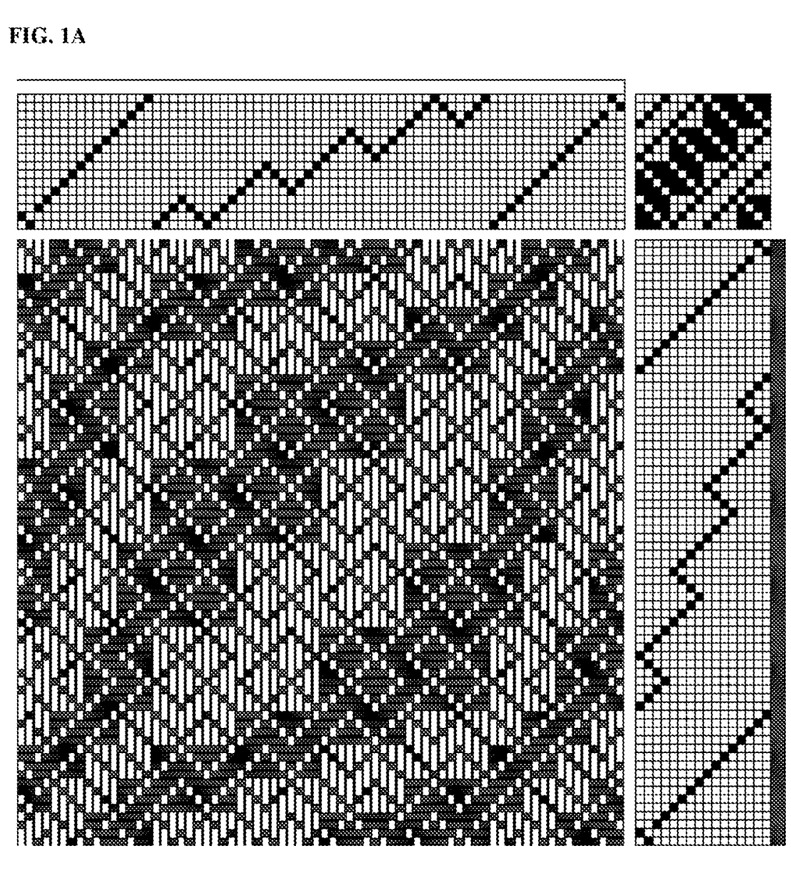
FIG. 1A shows a woven fabric with SAP fibers blended into both threads and yarns in the fabric.
Figure 1B:
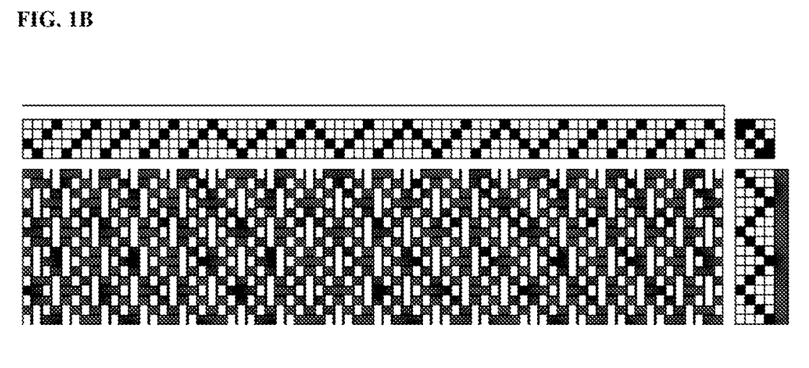
FIG. 1B shows an alternative woven fabric with SAP fibers blended into both threads and yarns in the fabric.
Figure 1C:
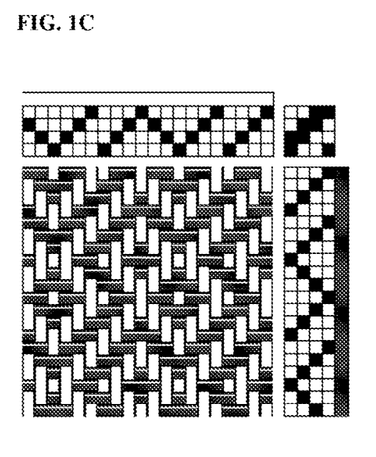
FIG. 1C shows a second alternative woven fabric with SAP fibers blended into both threads and yarns in the fabric.

As used herein, the terms "antimicrobial agent(s)" or "germicidal agent(s)" refer to materials (e.g., elemental silver) or chemicals or other substances that either kill or slow the growth of microbes. Among the antimicrobial agents or germicidal agents in use today are antibacterial agents (which kill bacteria), antiviral agents (which kill viruses), and antifungal agents (which kill fungi). A main category of antimicrobial agents are surface disinfectants, otherwise known as "biocides."

The term "biocides" is a general term describing a chemical agent, such as a pesticide, usually broad spectrum, which inactivates living microorganisms. Because biocides range in germicidal activity, other terms may be more specific, including "-static," referring to agents that inhibit growth (e.g., bacteriostatic, fungistatic, or sporistatic) and "-cidal," referring to agents that kill the target organism (e.g., bactericidal, fungicidal, sporicidal, or virucidal). Biocides have multiple targets and modes of action, which for instance, may include physical disruption and permanent damage to the outer cell membrane of a bacterial microbe. Some example of useful biocide chemistries include biguanides (e.g.: chlorohexidine, alexidine, polyhexamethylene biguanide, and relevant salts thereof), halogen-releasing agents (e.g.: iodine, iodophors, sodium hypochlorite, N-halamine, etc.), stabilized oxidants such as chlorine dioxide, stabilized peroxide (e.g., urea peroxide, mannitol peroxide) metal-containing species and oxides thereof (e.g.: silver, copper, selenium, etc. either in particle form or incorporated into a support matrix such as a zeolite or polymer), sulfides (e.g., sodium metabisulfite), bis-phenols (e.g., triclosan, hexachlorophene, etc), quaternary ammonium compounds (e.g., benzalkonium chloride, cetrimide, cetylpyridium chloride, quaternized cellulose and other quaternized polymers, etc.), various "naturally occurring" agents (e.g., polyphenols from green or black tea extract, citric acid, chitosan, anatase $TiO.sub.2$, tourmaline, bamboo extract, neem oil, etc.), hydrotropes (e.g., strong emulsifiers) and chaotropic agents (e.g., alkyl polyglycosides) and synergistic combinations thereof. Depending on substrate chemistry (polyolefin vs. cellulosic-based materials) and the method of incorporation into the product (topical vs. grafting), many of the above chemistries could be used alone or in concert to achieve the final claimed product properties of interest.

As used herein, the phrase "broad spectrum of microorganisms," is defined to include at a minimum Gram positive and Gram negative bacteria, including resistant strains thereof, for example methicillan-resistant *Staphylococcus aureus* (MRSA), vancomycin-resistant Enterococci (VRE) and penicillin-resistant *Streptococcus pneumoniae* (PRSP) strains. Preferably, it is defined to include all bacteria (Gram+, Gram– and acid fast strains) and yeasts such as *Candida albicans*. Most preferably, it is defined to include all bacteria (Gram+, Gram–, and acid fast), yeasts, and both envelope and naked viruses such as human influenza, rhinovirus, poliovirus, adenovirus, hepatitis, HIV, herpes simplex, SARS, and avian flu.

As used herein, the phrase "results in fewer viable pathogens on a treated surface compared to an untreated control surface" and the phrase "prevents or minimizes the contact transfer" are both defined to mean that the item in question will lead to at least a 0.5 log.sub.10 reduction in the transfer of a broad spectrum of viable microorganisms when contacting another surface as compared to an untreated control item as measured by the contact transfer protocol generally outlined in U.S. Patent Application Publication No. 2004/0151919, incorporated herein by reference with respect to the protocol, and described further in the Examples. Desirably, it leads to a reduction in viable microorganisms transfer by a factor of 1 log.sub.10. More desirably, it leads to a reduction in viable microorganisms transferred by a factor of 2 log.sub.10 or greater.

A "non-leaching" actives surface is one that passes ASTM E2149-01 testing protocol entitled "Standard Test Method for Determining the Antimicrobial Activity of Immobilized Antimicrobial Agents Under Dynamic Contact Conditions." The test is compatible with any actives merely by determining a target level and type of activity (e.g., chemical reduction, odor-emission, concentration of anti0inflammatant, etc.) and substituting that level of activity for antimicrobial activity. The lack of a zone of inhibition with the treatment agents chosen demonstrates the active species do not leach from the treated substrate, especially into skin in contact with a surface distal from the coated or embedded antimicrobial materials. Transcutaneous transfer may occur and is allowed to occur when the skin is in actual contact with the active antimicrobial agent. In a third set of experiments different coatings were tested for their efficiency against *E. coli*, American Type Culture Collection (ATCC) No. 8739 with both testing methods ASTM E2149-01 (dynamic contact test) and E2180-01 (static test for hydrophilic materials, Table 3). For ASTM E2149-01 two contact time points of 2 h and 24 h were chosen as to access short and long term effects. The film containing only film composition, without the fabric or additive to the fabric showed no change in bacteria concentration for both time points. Without being bound to theory, it is believed that the mechanism is not instantaneous but rather proceeds via a slow and steady bacteria destruction keeping in mind that for the reference film a 3-log CFU/ml increase was observed in the 24 hours experiment. Hence, the antimicrobial film has not only to struggle with the initial bacteria but also has to prevail over the bacteria's growth. For the static contact test ASTM E2180-01 the bacteria concentration for film sample containing the fabric antimicrobial additives increased by a factor of ten compared to the film composition reference, which could also be a superabsorbent polymer (SAP) film or powder.

As used herein, the term "apparel" refers to conventionally constructed wearing apparel that can be readily repositioned to overlay the mouth and nasal passages, such as turtle neck apparel, scarves, "Dickies" (which are turtleneck covers only, without the full upper body covering), bandanas, gators, and the like. Wraps without specific apparel structure, such as a handkerchief, patch, pocket and the like, may also be used.

One of the difficulties in providing fabric materials that are resistant to the growth of microbes or which can act to reduce the spread of microbes by filtering out and killing microbes that are attempting to pass through the fabric (in a gas or liquid medium) the fabric (in a gas or liquid medium) is the ability to control the antimicrobial activity over time and area in the fabric. Additionally, the provision of colors and visual patterns in the fabric can be diminished by after application of liquids to the fabric because of dye bleaching or pigment dissolution and bleeding from the applied antibiotics, which are usually carried in a liquid solvent. The present technology assists in overcoming or reducing many of these deficiencies.

The technology includes creation of a fiber or filament or yarn which can be woven into products alongside standard yarns that offer a high rate of efficacy in the killing of bacteria, virus/influenzas, fungi and other microbes before they can enter the respiratory track via nasal or oral routes. The fiber will have a constant state of mobility within its makeup.

This fiber can then be interwoven with other materials into products that are used daily by the general public, but have heretofore not been viewed as a health care benefit. These will include items such as, scarves, turtleneck sweaters and shirts, burkas, medical coverings, baby blankets, etc which will now capable of offering the additional protection of being antimicrobial in addition to their normal use. The classic medical masks offer no protection to the large majority of the population that will not use them for a variety of reasons, from stigma, appearance, lack of efficacy, to fashion and comfort The use of these new fibers in the creation of apparel or wearables that offer the public an increased level of protection will also allow for the economic and social interaction of society to continue by increasing the comfort level of the public when wishing to enter a heavily occupied area, such a grocery stores, shopping malls, events, or small gatherings in homes and offices.

A superabsorbent polymeric material is provided in fiber or filament form. The fibers (usually blended with other fibers to form threads or yarns or filaments, also blended to form fibers or yarns or knit directly into fine fabric may be, for example, from 0.01 to 100 decitex before addition to the other materials. SAP fibers tend not to have the tensile strength desirable for most usual fabric apparel (although some reduced tensile strength is acceptable in masks, covers and the like), and so the addition of the SAP fibers with stronger fibers is desirable. The other fibers should have a water absorbance that is less than 5% of the SAP fiber.

The SAP polymer can be easily imbibed with a controlled amount of aqueous borne antimicrobial material, either as a solute, suspension, dispersion or emulsions. The SAP generally has sufficiently open pores as to allow the somewhat larger molecular antimicrobials (e.g., silver particles, iodine crystals, etc.) to be carried into the SAP polymer network. The SAP fibers are then extruded or have the antimicrobial added after extrusion. Colorant may also be added at that time of extrusion or post-extrusion processing. After formation of the SAP fibers or filaments, those fibers or filaments may be processed into fabric along with other fabric fiber and materials as non-woven, woven, knitted or other manufactured fabric.

In forming threads and yarns, the individual threads may contain at least 0.5% total weight SAP within a single layer of fabric, and preferably from 1% to 75% of total threads in the fabric. The SAP fiber concentration in the final product should be from 1 to 50% by total weight of the fabric, 1 to 35% by total weight of the fabric or from 1 to 20% by total weight of the fabric. The actives agent in the SAP fiber or filament may be about 0.25% to 15% by weight of the SAP (solids or active liquids) and preferably is from 0.50% to 10% by weight of the SAP (solids or active liquids) in the individual SAP fibers or in the total fabric.

There are definite functional advantages for having the antimicrobials in the SAP and added before final fabrication of the fabric. There is the ability to better control the overall and/or local distribution of SAP and antimicrobials in the final fabric, as the SAP-bearing threads or yarns can be distributed as desired by known manufacturing techniques, such as timed feeding or positioned feeding of the SAP-bearing threads, yarns or filaments into the manufacturing process, whether forming non-woven fabrics or knitted or woven fabrics.

FIG. 1A shows a woven fabric 2 with SAP fibers 4 blended into both threads and yarns in the fabric.

FIG. 1B shows an alternative woven fabric 2B with SAP fibers 4 blended into both threads and yarns in the fabric.

FIG. 1C shows a second alternative woven fabric 2C with SAP fibers 4 blended into both threads and yarns in the fabric.

The distribution of the SAP fibers containing the antimicrobial agents can be readily seen from these FIGURES to be highly controllable in a final location in the fabric.

Germicidal Compositions

The germicidal compositions utilized may be one or more germicidal reagents. These reagents may be effective by themselves or may be combined to produce a synergistic effect that is non-additive of the individual components. These germicidal reagents may be further combined with processing aids and/or other ingredients that provide functional properties to the compositions. Exemplary germicidal compositions may be based on cationic polymers, such as quaternary ammonium compounds and polymeric biguanides, alcohols, and surfactants. Combinations of cationic polymers such as quaternary ammonium compounds (e.g., quaternary ammonium cellulose and quaternary ammonium siloxane), polymeric biguanides, surfactants, alcohols, and organic acids, such as acetic, citric, benzoic acids, may produce non-additive, synergistic systems with broad pathogen efficacy. The combinations with other germicidal compounds, surfactants, appear to improve germicidal efficacy of polymeric biguanides over treatments with that employ polymer biguanides alone. Poly-hexamethylene biguanide (PHMB) hydrochloride is an exemplary cationic biguanide that is useful for providing germicidal surface-covering assemblies. Commercially available versions of PHMB, such as under the trade names Cosmocil CQ (20 wt. % PHMB in water) or Vantocil, a heterodisperse mixture of PHMB with a molecular weight of approximately 3,000 grams/mole, are active against gram-positive and gram-negative bacteria, but may not be sporicidal. Additional active germicidal agents may include, but are not limited to, a quaternary ammonium compound, a quaternary ammonium siloxane, a polyquaternary amine; metal-containing species and oxides thereof, either in particle form or incorporated into a support matrix or polymer; halogens, a halogen-releasing agent or halogen-containing polymer, a bromo-compound, a chlorine dioxide, a thiazole, a thiocynate, an isothiazolin, a cyanobutane, a dithiocarbamate, a thione, a triclosan, an alkylsulfosuccinate, an alkyl-aminoalkyl glycine, a dialkyl-dimethyl-phosphonium salt, a cetrimide, hydrogen peroxide, 1-alkyl-1,5-diazapentane, or cetyl pyridinium chloride.

Table 1 summarizes various biocides and processing aids that may be used in germicidal compositions that can be used to make the germicidal surface-covering assembly. It also lists their common chemical names or commercial names. Quaternary ammonium compounds, such as commercially available under the names of Aegis™ AEM 5700 (Dow Corning, Midland, Mich.) and Crodacel QM (Croda, Inc., Parsippany, N.J.), with certain surfactants such as alkyl-polyglycosides, available commercially under the name Glucopon 220 UP (Cognis Corp, Ambler, Pa.), and chitosan glycolate, available under the name Hydagen CMF and Hydagen HCMF (Cognis Corp., Cincinnati, Ohio), can significantly enhance the killing efficacy of PHMB in a synergistic fashion as will be demonstrated in the tables herein. One should note that many of the biocides described herein may be used singly or in combination in a variety of products which vary considerably in activity against microorganisms. TABLE-US-00001 TABLE 1 Table of Active Reagents and Processing Aids Concentration Reagent Range (wt. %) Brand or Common Name Vendor Name Polyhexamethylene biguanide (PHMB) 0.01-20 Cosmocil CQ Arch Chemicals, Inc. Norwalk, Conn. Chitosan glycolate 0.01-10 Hydagen CMF and HCMF Cognis Corp., Ambler, Pa. Octadecylaminodimethyl Trimethoxysilylpropyl 0.01-10 AEGIS AEM 5700 Dow-Corning, Ammonium Chloride Midland, Mich. N-Alkyl Polyglycoside 0.01-10 Glucopon 220 UP Cognis Corp., Ambler, Pa. PG-Hydroxyethylcellulose Cocodimonium 0.01-10 Crodacel QM Croda Inc., Chloride (Quaternary Ammonium Persipanny, N.J. CellulosicSalt) Xylitol 0.01-10 Xylitol Sigma-Aldrich, Milwaukee, Wis. 2-hydroxy-1,2,3-propanetricarboxylic acid 0.01-10 Citric Acid Hach Company Ames, Iowa Benzenecarboxylic acid 0.1-2.0 Benzoic acid Mallinckrodt Baker, Inc Phillipsburg, N.J. 2-hydroxybenzoic acid 0.01-10 Salicylic acid Mallinckrodt Baker, Inc Phillipsburg, N.J. Methane-carboxylic acid 0.01-2.0 Acetic acid Sigma-Aldrich St. Louis, Mo. 1,3-Propanedicarboxylic Acid 0.01-10 Glutaric acid Sigma-Aldrich St. Louis, Mo. Iodine 0.05-10 Iodine Sigma-Aldrich St. Louis, Mo. Ethyl Hydroxyethyl cellulose 0.01-5.0 Bermocoll EBS 481 FQ Akzo Nobel, Inc., ("E 481") Stamford, Conn. Polyvinyl pyrrolidone 0.01-10 Plasdone K90 ISP Technologies, Inc., Wayne, N.J. Poly(vinyl pyrrolidone-co-vinyl acetate) 0.01-10 PVP/VA S-630 ISP Technologies, Inc., Wayne, N.J. Polyvinyl pyrrolidone-Iodine complex 0.01-10 PVP-Iodine ISP Technologies, Inc., Wayne, N.J. Guanidine Hydrochloride and Sorbitol 0.01-5.0 Nicepole FL NICCA USA, Inc. Fountain Inn, S.C. Acrylic Co-Polymer Compound and Isopropyl 0.01-5.0 Nicepole FE 18U NICCA U.S.A., Inc. Alcohol Fountain Inn, S.C. 25% Copper oxide (CuO, Cu.sub.2O) 0.01-20.0 Cupron, Cupron, Inc. (CAS #1317-39-1), 75% polypropylene Greensboro, N.C. (PP) resin Silver Sodium Hydrogen Zirconium 0.01-20.0 AlphaSan® RC 2000*Milliken, Phosphate Spartanburg, S.C. Silver Zinc glass (70-100%) barium sulfate 0.01-20.0 Irgaguard B 7520 Ciba Specialty Chemicals Corp. (1-30%), PP resin (10-30%) Tarrytown, N.Y. These additives have been typically compounded in thermoplastic # resins (e.g., polypropylene (PP)) to produce a concentrate which is then dry blended with the # virgin resin and co-extruded to produce fibers and webs containing such additives.

These polymeric structure formats are a problem according to the technology in use. The present invention requires the materials to be in a carrier that can be sufficiently wetted by moisture vapor from exhalation so that the surface of the substrate is moist or even liquid, as with lower molecular weight hydrophilic or even aqueous-soluble polymers such as polyvinyl alcohols (10,000 to 50,000 number average molecular weight), polyvinylidene chloride (9,000 to 50,000 number average molecular weight) Concentration of the antimicrobial additive should be on the surface of the carrier even though this depends on several factors including additive concentration in the melt relative to the main body of resin or type of resin, processing/application conditions and thermal history, etc.

In certain embodiments the germicidal composition includes combinations of biocide active agents that work against both bacteria and viruses. For instance, a composition may include: PHMB, quaternary ammonium cellulose, xylitol, citric acid, benzoic acid, surfactant, complexing agent (e.g., PVP), and/or antistatic agent (e.g., Nicepole FL). A desirable antistatic agent is one that does not reduce surface tension of water by more than 20 dynes/cm. The present composition desirably is moderately hydrophilic; hence, a droplet of a formulation applied to a surface can produce a contact angle of less than about 90° with respect to, for example, a polypropylene substrate surface. The compositions have a pH in a range of about 2 to about 5 or 6. Preferred pH ranges are about 2.5-4, or 2.5-3.5, depending on the desired, particular environmental conditions for use. The compositions may also contain an acrylic co-polymer compound and isopropyl alcohol, which serves as an antistatic agent useful for treating nonwoven fabrics such as those commonly found in medical fabrics.

A germicidal solution may contain a primary microbial active agent, for example, 0.1-99.9 wt % polyhexamethylene biguanide (PHMB) by weight of active agents, and a secondary active agent selected from at least one of the following: alkyl polyglycosides, quaternized cellulose derivatives, quaternized siloxanes, surfactants, and organic acids. The final concentration for each of the active reagent and processing aids on a treated substrate can range from about 0.01-20 wt %. The exact concentrations may depend on the specific kind of microorganism that one is targeting against and/or the nature of the coated substrate material.

The germicidal composition may be odorless to humans; that is, the composition is undetectable at least to the human olfactory system. This characteristic is important if the germicidal composition is to be used on face masks and other substrates that come into close proximity to the human nose.

Substrates

The apparel substrates used in the practice of the present technology must be porous enough to allow wearers to breathe through the fabric without excessive air flow being drawn parallel to the surface of the fabric in the apparel. Otherwise the air would be drawn around, rather than through, the apparel. This is another advantage of using a repositionable fabric apparel element such as a turtle neck. The neck may be pulled over the lower portions of the face and adjusted easily into a comfortable position that best control flow through, and not around the fabric. Generally speaking, the treated surface of the germicidal surface-covering assembly would be outward or exterior facing and away from the skin-contacting surface such as a lining of a garment or article, although internal compositions work well also. The purpose of this orientation is to address the indirect transmission or the contact transfer of pathogens.

The material may have a natural and significant elasticity, or may be a material with low elastic stretchability or memory, such as a tightly woven fabric with less than 5% elastic elongation or a loosely woven fabric with 15-20% elongation in at least one direction. The elongation may also be created by the elastic nature of the fabric composition itself or by added elements such as elastic edges or inserts. Taughtness in an applied position may be also provided in whole or in part by fabric closure systems such as ties, belts, velour and crochet (e.g., Velcro™ attachments) and adhesive.

Generally speaking, nonwoven materials treated with the germicidal compositions may even largely maintain their liquid barrier properties when segregated to the surface of the materials, as the moisture flow through the fabric may wet or moisten the carrier (which is preferably in addition to the fabric structural material) and acts as a moisture holder or even liquid/pasty film forming layer actively supporting and presenting the antimicrobial agent. It is believed that by means of controlling the topical placement of the antimicrobial composition, in which the agents are confined to the outermost or top spunbond layer of a substrate, for instance, one can enhance the creation of a liquid conduit or liquid support in the layers of the substrate material, thereby achieving the beneficial combination of retention of particles (e.g., viruses) and germicidal properties. In addition, placing the germicidal chemistry on the surface of the substrate will make the biocides more readily available to interact with pathogens, thus improving overall efficacy.

Process Methods

The germicidal compositions can be applied topically to the external surfaces of the fabric, which may be knitted, woven or nonwoven web filaments, yarns or final fabrics after they are formed. Desirably, an even, but not necessarily exactly uniform coating is applied over the substrate surfaces. The coating has a relatively even distribution over or within the treated substrate surface. Any processing aid may evaporate or flash off once the germicidal composition dries on the substrate surface, but the coated composition must or should retain its hydrophilic and even hygroscopic ability so that a liquid or floating layer that attracts and holds particles is formed on fabric internal and/or external surfaces. Suitable processing aids may include alcohols, such as isopropanol, butanol, hexanol or octanol.

The active compositions should comprise as a single layer or blended layer or combinations of layers at least the antimicrobial agent, a water-absorbing or water-holding component (WHA), a surfactant, and other possible ingredients. It is preferred that the WHA be hygroscopic, a term understood in the art as requiring that the material active withdraw moisture from air in contact with the material. Materials such as commercially available super-absorbent polymers, humectants, hygroscopic salts (particularly in water soluble polymers), glycerine, viscous sugar solutions (mannitol, rabbitol included as higher molecular weight, less volatile sugar solutions), and the like.

The materials described herein may be part of or the entirety of materials used as clothing, coverings (e.g., wraps and blankets, sheets, pillow cases, surgical drapes, equipment such as backpacks, hoods, jackets, shirts, dental tray covers, sheets on trays for carrying or supporting devices that should be kept free of active microbes, and the like) and articles.

According to an embodiment, the antimicrobial composition(s) and associated materials in the same or adjacent layer can be applied to the material substrate via conventional saturation processes such as a so-called "dip and squeeze" or "padding" technique. The "dip and squeeze" or "padding" process can coat both sides of and/or through the bulk of the substrate with the germicidal composition. When dipped in a bath, the germicidal solution be a unitary medium containing all components, or in subsequent multiple step processing, other desired components may be later added to the base germicidal layer. For instance, a formulation of a unitary germicidal solution may include leveling and/or antistatic agents. On substrates containing polypropylene, an antistatic agent can help dissipate static charge build-up from mechanical friction. An antistatic agent can be added to the germicidal solution, and the mixture can be introduced simultaneously to the material substrate in one application step. Alternatively, the antistatic solution can be applied using a spray after the germicidal solution in a second step. The antimicrobial material may also be dusted over a wet carrier layer on the substrate and that will fix the antimicrobial on the surface. Comparative test results were as follows for the inventive materials:

TABLE 1

Pressure Drop of Medtextra ® Fabrics Media Grades

| Media Grade | | dP (mm H$_2$O) | |
|---|---|---|---|
| Basis Weight (gsm) | % SAF | @20% RH | @50% RH |
| 100 | 2.4% | 1.2 | 2.4 |
| 30 | 4.0% | 0.5 | 1.6 |
| 52 | 4.6% | 0.8 | 2.0 |
| 75 | 4.8% | 1.5 | 2.6 |

TABLE 1-continued

Pressure Drop of Medtextra ® Fabrics Media Grades

| Media Grade | | dP (mm H₂O) | |
|---|---|---|---|
| Basis Weight (gsm) | % SAF | @20% RH | @50% RH |
| 80 | 3.0% | 1.7 | 2.9 |
| 139 | 5.2% | 3.1 | 4.4 |

TABLE 2

Penetration Values (1 - Efficiency)

| Basis wt. SAP Rel. Humidity | 100 gsm 2.4% 20% | 50% | % Improved | 52 gsm 4.60% 20% | 50% | % Improved | 75 gsm 4.80% 20% | 50% | % Improved | Overall AVG |
|---|---|---|---|---|---|---|---|---|---|---|
| Particle Size | | | | | | | | | | |
| 1.6-2.2 | 100.0% | 83.5% | 16.5% | 100.0% | 83.4% | 16.6% | 100.0% | 81.1% | 18.9% | 17% |
| 2.2-3.0 | 100.0% | 70.8% | 29.2% | 100.0% | 71.8% | 28.2% | 100.0% | 67.0% | 33.0% | 30% |
| 3.0-4.0 | 88.7% | 59.9% | 32.5% | 100/0% | 62.5% | 37.5% | 87.9% | 53.8% | 38.8% | 36% |
| 4.0-5.5 | 75.8% | 58.8% | 22.5% | 86.5% | 62.3% | 28.0% | 70.8% | 52.9% | 25.3% | 25% |
| 5.5-7.0 | 73.0% | 58.5% | 19.8% | 86.2% | 63.8% | 26.0% | 66.9% | 52.8% | 21.0% | 22% |
| 7.0-10.0 | 52.8% | 42.2% | 20.1% | 72.8% | 49.5% | 32.1% | 49.9% | 38.4% | 23.0% | 25% |
| AVG particle size in microns | | | 23% | | | 28.% | | | 27% | 26% |

When compared to the 100-gsm media with 2.4% superabsorbent fiber, equivalent filtration efficiency is achieved for 1.6-3.0 micron particles using the 52-gsm media with 4.6% superabsorbent fiber. In this case, a small increase in superabsorbent fiber allows for an almost 50% reduction in overall fiber use. In addition, the air resistance seen for the 52-gsm media was 2.03-mm of water while the air resistance for the 100-gsm prototype was 2.4-mm of water, almost 20% higher. When the overall basis weight is increased from 52-gsm to 75 gsm, superior.

In certain product forms, where one wishes to treat only a single side and not only the inner layers that make up a fabric substrate or opposing side of the sheet substrate, in which the substrate material any layered to another sheet ply (e.g., filter or barrier media) that is without the antimicrobial treatment, other processes are preferred such as at rotary screen, reverse roll, Meyer-rod (or wire wound rod), Gravure, slot die, gap-coating, or other similar techniques, familiar to persons in the printing and textile industry. Also one may consider printing techniques such as flexographic, ink jet, bubble jet or digital techniques. Alternatively one may use a combination of more than one coating to achieve a controlled placement of the treatment composition. Such combination may include, but not limited to, a reverse Gravure process followed by a Meyer rod process. Alternatively, the germicidal composition may be applied through an aerosol spray on the substrate surface. The spray apparatus can be employed to apply the germicidal solution and/or antistatic agent only on one side of the substrate sheet or on both sides separately if desired. An antistatic agent can be applied to the substrate in a secondary step, for example, using a spray system or any other conventional application process.

Various other methods may be employed for contacting and/or creating or attached to a substrate(s) with the treatment composition or compositions in accordance with the invention. For example, a substrate may be printed on by means of print rolls or other coating steps, or spray techniques may be employed. Preferably, the treatment composition or compositions are applied as an overlayer onto the substrate by a Meyer rod, reverse Gravure or flexographic techniques, for example, in such a way that the treatment composition forms a uniform and homogeneous layer on top of the substrate with minimum penetration of the treating composition into the bulk of the substrate. The overlayer coating, in general, results in more uniform distribution of the anti-microbial treatment on the substrate and permits the anti-microbial agent(s) to be more readily available on the surface of the substrate, although it is preferred to have the antimicrobial material distributed with its carrier throughout the apparel fabric to provide greater surface area for catching and holding the virus particles.

Germicidal Test Method

A. Sample Preparation

Test organisms are grown in 25 mL appropriate broth medium for about 24.+-0.2 hours at 37.+-0.2° C. in a orbital shaker. The bacterial culture is then transferred by placing about 100.mu.L aliquot in 25 mL of broth and grown again for about 24.+-0.2 hours at 37.+-0.2° C. The organisms are then centrifuged and washed three times with phosphate buffered saline (PBS). The organisms are then suspended in PBS to obtain an inoculum of approximately $1 \times 10^8$ CFU/mL.

The test articles and control swatches are exposed to an ultraviolet light source for about 5-10 minutes per side before testing to assure that the swatches are sanitized prior to inoculation with the bacteria. The test materials are brought into contact with a known population of test bacteria from the inoculum for a specified period of time. A sample is then plated at the end of the exposure time to enumerate the surviving bacteria. The log.sub.10 reduction from the control material and the original population is calculated using the following formula: Log.sub.10 Control*–Log$_{10}$ CFU/swatch Test Article=Log$_{10}$ Reduction*CFU/swatch from control swatches or theoretical CFU/swatch.

After exposing the bacteria to the surface of a treated product for a designated amount of time (.about.40 seconds), the substrate is placed in a flask and a buffer solution is added to elute the microorganisms off the substrate prior to plating them to see how many are left alive. This buffer solution contains a chemical to de-activate or "neutralize" the germicidal agent to (a) stop the active agent from killing the organisms after the designated time period and (b) to prevent artifacts that may arise from exposing the microorganisms to the germicidal in solution rather than solely on the substrate. The neutralizer is pre-screened to make sure that they do not affect the microorganisms. The neutralizer employed may be selected from a list that is commonly used in the field. These include non-ionic detergents, Bisulphate, lecithin, Leethen broth, thiosulfate, thioglycollate, and pH buffers. Method similar to those described in American Society for Testing and Materials, Standard Practices for Evaluating Inactivators of Germicidal Agents Used in Disinfectant, Sanitizer, Antiseptic, or Preserved Products, Amer. Soc. Testing Mat. E 1054-91 (1991) can be used.

B. Contact Transfer Protocol

The following generalized discussion relates to a method for determining viable microbe transmission levels or contact transfer of microbes from one contaminated article to at least one other article. Generally speaking, the method includes applying an inoculum including a microbe to a first surface, contacting a transfer substrate to the first surface, extracting the transferred inoculum from the transfer substrate, permitting the extracted inoculum to incubate, and quantifying the microbe level to determine a percent recovery. As used herein, "inoculum" refers to any material containing at least one microbe that may act as a source of infection in a host.

The method may be used to measure viable contact transfer of various microbes, including, for example, *Aspergillus niger* (American Type Culture Collection (ATCC®) No. 16404), *Candida albicans* (ATCC® No. 10231), Hepatits A HM175/18f (ATCC® No. VR-1402), Herpes simplex virus 1 GHSV-UL46D (ATCC® No. VR-1545), *Acinetobacter baumannii* (ATCC® No. 15149), *Clostridium* difficle (ATCC® No. 43594), *Enterobacter cloacae* (ATCC® No. 29249), *Enterococcus faecalis* (ATCC® No. 51299), *Enterococcus faecium* (ATCC® NO. 700221), *Enterococcus hirae* (ATCC® No. 10541), *Escherichia coli* (ATCC® No. 13706), *Escherichia coli* (ATCC® No. 31705), *Mycobacterium smegmatis* (ATCC® No. 10143), *Mycobacterium tuberculosis* (ATCC® 27294), *Pseudomonas aeruginosa* (ATCC® No. 9027), *Pseudomonas aeruginosa* (ATCC® No. 27853), *Staphylococcus aureus* (ATCC® No. 6538), *Staphylococcus aureus* (ATCC® No. 33592), *Staphylococcus epidermidis* (ATCC® No. 12228), and *Staphylococcus epidermidis* (ATCC® No. 51625).

After the desired microbe is selected, an inoculum is prepared by diluting a stock culture of the microbe. The culture may be diluted to any desired level using a sterile buffered liquid, and in some instances, may be diluted to an inoculum level of from about $1 \times 10^6$ colony forming units (CFU)/ml to about $3 \times 10.^6$ CFU/ml. However, for the present testing, the inoculum level was $5 \times 10^8$ CFU/ml. Prior to performing the evaluation, a sterile buffer solution may be prepared for later use. The buffer solution may be replaced about every two months. In some instances, the buffer solution may be sterile phosphate buffered water. The desired inoculum is then placed aseptically onto a first surface. Any quantity of the desired inoculum may be used. However, for the contact transfer testing of the germicidal surface-covering assembly, a quantity of about 0.5 ml is applied to the first surface. Furthermore, the inoculum may be applied to the first surface over any desired area. In some instances, the inoculum may be applied over an area of about 7 inches (178 mm) by 7 inches (178 mm). However, in the present testing, the inoculum is applied to substantially all of a 4 inch (101 mm) by 4 inch (101 mm) square piece of material that constitutes the first surface.

The innoculum is then permitted to remain on the first surface for a relatively short amount of time. For example, about 20 seconds before the article to be evaluated, i.e., the transfer substrate is brought into contact with the first surface.

The transfer substrate may be any apparel as defined herein that is worn about the head (bandana, headband, etc) or neck (scarf, "Dickie" or turtleneck apparel. Masks may also be used, but the apparel is an approved embodiment as it may be repositioned from its normal use.

The solution on the sample plates may then be incubated for a desired amount of time to permit the microbes to propagate. In some instances, the solution may incubate for at least about 48 hours. The incubation may take place at any optimal temperature to permit microbe growth, and in some instances may take place at from about 33° C. to about 37° C. In some instances, the incubation may take place at about 35° C. After incubation is complete, the microbes present are counted and the results are reported as CFU/ml. The percent recovery may then be calculated by dividing the extracted microbes in CFU/ml by the number present in the innoculum in (CFU/ml), and multiplying the value by 100.

The technology included herein also include a method for the manufacture of a fabric having antimicrobial activity with steps that might include
 a) providing a superabsorbent polymer composition;
 b) associating an antimicrobial composition into the superabsorbent polymer composition to form a final composition;
 c) extruding the final composition to form active fibers or active filaments;
 d) blending the active fibers or active filaments with textile fibers or textile filaments to form a textile blend; and
 e) fabricating the textile blend to form a final fabric material having antimicrobial activity.

The antimicrobial composition preferably comprises a quaternary ammonium salt and may further comprises a humectant. Fabricating the textile blend may comprise forming a non-woven fabric comprising the textile blend. The textile blend may be distributed with at least 20% by weight higher concentrations of the textile blend in some areas of the final fabric material than other areas of the final fabric material so that there is greater antimicrobial activity in some areas of the final fabric material than in other areas. The fabricating of the textile blend may includes weaving or knitting a final fabric comprising the textile blend.

The present invention has been described in general and in detail by way of examples. The words used are words of description rather than of limitation. Persons of ordinary skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein and the appended claims should not be limited to the description of the preferred versions herein.

What is claimed:

1. A fabric for delivering active ingredients to a surface when that fabric is positioned against the surface, the fabric comprising a moisture vapor porous combination of fabric materials, and the fabric comprises at least 0.5% by total weight of at least one layer of the fabric of a superabsorbent polymer fiber, and the superabsorbent polymer fiber contains an absorbed aqueous reservoir of an aqueous liquid solution carrying the active ingredients, and wherein the superabsorbent fiber has a coating on its surface through which the liquid solution in the absorbed aqueous reservoir can migrate or flow, carrying the active ingredients onto an exposed surface of the superabsorbent polymer fiber, so that the active ingredients in the liquid solution on the surface of the superabsorbent polymer can react or interact with an environment in contact with the active ingredients in the liquid solution on the surface of the superabsorbent polymer fiber.

2. The fabric of claim 1 wherein the coating on the surface of the superabsorbent polymer acts as a carrier that is able to absorb sufficient moisture from an ambient environment of 50% relative humidity, 760 mm of air pressure and 20 degrees Centigrade to maintain a wet surface on the carrier from which active ingredients are transferred to the environment in contact with the active ingredients on the surface of the superabsorbent polymer.

3. The fabric of claim 1 wherein the active ingredients are selected from the group consisting of anti-inflammatants, analgesics, antiperspirants, odor-reducing compounds, stain reducing agents, moisturizing agents, skin-cooling compounds, and fragrances.

4. The fabric of claim 1 wherein the coating on the surface of the superabsorbent polymer comprises a hydrophilic material.

5. The fabric of claim 2 the coating on the surface of the superabsorbent polymer comprises a hydrophilic material.

6. The fabric of claim 3 wherein the coating on the surface of the superabsorbent polymer comprises a hydrophilic material.

7. The fabric of claim 4 wherein the coating on the surface of the superabsorbent polymer comprises a water-soluble polymer.

8. The fabric of claim 5 wherein the coating on the surface of the superabsorbent polymer comprises a water-soluble polymer.

9. A method of reducing adverse effects in an environment around an environmental surface comprising placing the fabric of claim 1 on the environmental surface and exposing the fabric to ambient moisture vapor to cause the superabsorbent polymer fiber to absorb water from the ambient moisture vapor and dynamically transmit active ingredients in the reservoir onto the surface of the superabsorbent polymer fiber.

10. The method of claim 9 wherein the environment surface comprises the skin of a human, and the fabric comprises apparel.

11. A material for application of active ingredients to a human body where there is an expected flow of high humidity or moisture, the material comprising a fabric in the shape of apparel including at least one layer in the apparel of a moisture-vapor porous combination of fabric materials, and the fabric comprises at least 0.5% by total weight of at least one layer of the fabric of a superabsorbent polymer fiber, and the superabsorbent polymer fiber contains an absorbed aqueous reservoir of an aqueous liquid solution carrying the active ingredients, and wherein the superabsorbent fiber has on its surface, an aqueous penetrable layer through which a liquid in the absorbed aqueous reservoir can migrate or flow, carrying the active ingredients onto an exposed surface of the superabsorbent polymer fiber, so that the active ingredients on the surface of the superabsorbent polymer retained in the liquid can react or interact with an environment in contact with the active ingredients retained in the liquid.

12. The fabric of claim 11 wherein the solution also includes a hygroscopic material.

13. The fabric of claim 12 wherein the surface of the superabsorbent fibers have a discontinuous coating on the superabsorbent fiber which restricts flow off the superabsorbent fiber.

14. The fabric of claim 12 wherein the surface of the superabsorbent fibers have a discontinuous coating on the superabsorbent fiber which restricts flow off the superabsorbent fiber.

15. The fabric of claim 13 wherein the surface of the superabsorbent fibers have a discontinuous coating on the superabsorbent fiber which restricts flow off the superabsorbent fiber.

16. The fabric of claim 15 wherein the surface of the superabsorbent fibers have a discontinuous coating on the superabsorbent fiber which restricts flow off the superabsorbent fiber.

* * * * *